United States Patent
Higashi et al.

(10) Patent No.: US 12,283,375 B2
(45) Date of Patent: Apr. 22, 2025

(54) REMOTE CONTROL DEVICE, AND REMOTE CONTROL SYSTEM

(71) Applicant: NIHON KOHDEN CORPORATION, Tokyo (JP)

(72) Inventors: Kazuri Higashi, Tokorozawa (JP); Ryota Auchi, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 17/279,853

(22) PCT Filed: Sep. 26, 2019

(86) PCT No.: PCT/JP2019/037962
§ 371 (c)(1),
(2) Date: Mar. 25, 2021

(87) PCT Pub. No.: WO2020/067339
PCT Pub. Date: Apr. 2, 2020

(65) Prior Publication Data
US 2022/0037015 A1    Feb. 3, 2022

(30) Foreign Application Priority Data
Sep. 28, 2018    (JP) .................. 2018-184191

(51) Int. Cl.
*G16H 40/67*    (2018.01)
*G06F 3/01*    (2006.01)
(Continued)

(52) U.S. Cl.
CPC ............. *G16H 40/67* (2018.01); *G06F 3/017* (2013.01); *G08B 25/008* (2013.01); *G08C 17/02* (2013.01);
(Continued)

(58) Field of Classification Search
CPC ...... G16H 40/67; G06F 3/017; G08B 25/008; G08C 17/02; G08C 2201/31; G08C 2201/32
(Continued)

(56) References Cited

U.S. PATENT DOCUMENTS 5,877,880 A * 3/1999 Kuo .................. H04B 10/1143
398/129
9,545,287 B2 * 1/2017 Tashiro .................. A61B 34/25
(Continued)

FOREIGN PATENT DOCUMENTS

| CN | 105270294 A | 1/2016 | |
|---|---|---|---|
| CN | 106781402 A * | 5/2017 | ............. G08C 17/02 |

(Continued)

OTHER PUBLICATIONS

International Search Report (PCT/ISA/210) dated Nov. 18, 2019 issued by the International Searching Authority in International Application No. PCT/JP2019/037962.
(Continued)

*Primary Examiner* — Stephen S Hong
*Assistant Examiner* — Broderick C Anderson
(74) *Attorney, Agent, or Firm* — Sughrue Mion, PLLC

(57) ABSTRACT

A memory stores gesture information corresponding to a gesture of a medical worker that is allocated to a function of a medical device. A sensor is configured to detect a gesture. A transmitter is configured to wirelessly transmit a control signal for remotely controlling the function. A processor is configured to cause the transmitter to transmit the control signal in a case where the gesture corresponding to the gesture information is detected by the sensor.

9 Claims, 5 Drawing Sheets

(51) Int. Cl.
  *G08B 25/00* (2006.01)
  *G08C 17/02* (2006.01)
(52) U.S. Cl.
  CPC ..... *G08C 2201/31* (2013.01); *G08C 2201/32* (2013.01)
(58) Field of Classification Search
  USPC .......................................................... 715/863
  See application file for complete search history.

(56) References Cited

U.S. PATENT DOCUMENTS

| | | | | |
|---|---|---|---|---|
| 2003/0149803 | A1* | 8/2003 | Wilson | G06F 3/0346 710/1 |
| 2007/0229250 | A1 | 10/2007 | Recker et al. | |
| 2007/0283296 | A1 | 12/2007 | Nilsson | |
| 2008/0114226 | A1* | 5/2008 | Music | A61B 5/14551 600/323 |
| 2008/0312584 | A1 | 12/2008 | Montgomery et al. | |
| 2009/0251352 | A1* | 10/2009 | Altonen | H01H 9/02 341/176 |
| 2009/0282371 | A1* | 11/2009 | Curl | G16H 40/60 704/275 |
| 2010/0131280 | A1* | 5/2010 | Bogineni | G10L 15/22 704/275 |
| 2013/0176230 | A1 | 7/2013 | Georgiev et al. | |
| 2014/0195986 | A1* | 7/2014 | Li | G06F 3/005 715/862 |
| 2015/0305813 | A1 | 10/2015 | Tashiro | |
| 2018/0196501 | A1 | 7/2018 | Trotta | |
| 2019/0038236 | A1* | 2/2019 | Hays | A61M 16/022 |
| 2020/0019235 | A1 | 1/2020 | Trotta | |

FOREIGN PATENT DOCUMENTS

| | | |
|---|---|---|
| CN | 206906811 U | 1/2018 |
| CN | 108287608 A | 7/2018 |
| EP | 1 498 082 A1 | 1/2005 |
| EP | 2 189 977 A2 | 5/2010 |
| JP | 2002-112368 A | 4/2002 |
| JP | 2014-180337 A | 9/2014 |
| JP | 2018-102671 A | 7/2018 |
| WO | 2007/138393 A2 | 12/2007 |
| WO | 2014/183792 A1 | 11/2014 |
| WO | 2015/012006 A1 | 1/2015 |

OTHER PUBLICATIONS

Written Opinion (PCT/ISA/237) dated Nov. 18, 2019 issued by the International Searching Authority in International Application No. PCT/JP2019/037962.

Office Action issued Jan. 18, 2022 by the Japanese Patent Office in counterpart Japanese Patent Application No. 2018-184191.

Office Action issued Mar. 27, 2023 by the China National Intellectual Property Administration in corresponding CN Patent Application No. 201980063771.6.

Office Action issued Mar. 30, 2023 by the European Patent Office in counterpart European Patent Application No. 19787485.2.

* cited by examiner

REMOTE CONTROL DEVICE, AND REMOTE CONTROL SYSTEM

CROSS-REFERENCE TO RELATED APPLICATIONS

This application is a National Phase Entry of PCT International Application No. PCT/JP2019/037962, filed on Sep. 26, 2019, which claims priority to Japanese Patent Application No. 2018-184191 filed on Sep. 28, 2018.

TECHNICAL FIELD

The presently disclosed subject matter relates to a remote control device for remotely controlling functions of a medical device. The presently disclosed subject matter also relates to a remote control system including the medical device and the remote control device.

BACKGROUND ART

Japanese Patent Publication No. 2018-102671A discloses a vital sign information monitor as an example of the medical device. The vital sign information monitor is disposed beside a patient or a subject, so that a sensor or the like attached on the patient or the subject is connected to the vital sign information monitor. The vital sign information of the patient or the subject acquired through the sensor is used for monitoring or display by the vital sign information monitor. When the vital sign information indicates a deviation from a normal state of the patient or the subject, the vital sign information monitor outputs an alarm to perform notification to a medical worker. The medical worker cancels the notifying operation by inputting a predetermined instruction to the vital sign information monitor.

In the case of the vital sign information monitor as described above, it is necessary to go to the installation location of the vital sign information monitor and input an instruction for canceling the notifying operation every time an unexpected notifying operation occurs. Therefore, it is inevitable that the performance of the therapeutic action and the nursing work is degraded. The degradation becomes remarkable particularly in operating rooms, neonatal intensive care units (NICU), and other environments where increased cleanliness is required. This is because it is necessary to disinfect fingers and the like every time the manipulation of the vital sign information monitor is performed.

It is thus demanded to suppress the degradation in the performance of a therapeutic action or a nursing work caused by the manipulation of a medical device.

SUMMARY OF INVENTION

An illustrative aspect of the presently disclosed subject matter provides a remote control device comprising:
 a memory storing information corresponding to at least one of a gesture, voice, and a physical feature of a medical worker that is allocated to a function of a medical device;
 a sensor configured to detect at least one of a gesture, voice, and a physical feature;
 a transmitter configured to wirelessly transmit a signal for remotely controlling the function; and
 a processor configured to cause the transmitter to transmit the signal in a case where the at least one of the gesture, the voice, and the physical feature corresponding to the information is detected by the sensor.

An illustrative aspect of the presently disclosed subject matter provides a remote control system comprising:
 a medical device; and
 a remote control device configured to remotely control a function of the medical device,
 wherein the medical device comprises:
 a memory storing information corresponding to at least one of a gesture, voice, and a physical feature of a medical worker that is allocated to the function;
 a sensor configured to detect at least one of a gesture, voice, and a physical feature;
 a transmitter configured to wirelessly transmit a signal for remotely controlling the function; and
 a processor configured to cause the transmitter to transmit the signal in a case where the at least one of the gesture, the voice, and the physical feature corresponding to the information is detected by the sensor.

According to the configuration as described above, since the remote control device wirelessly transmits the signal for controlling the function of the medical device by sensing at least one of the gesture, the voice and the physical feature of the medical worker, the medical worker can control the function of the medical device with the minimum necessary action without directly touching the remote control device or the medical device. As a result, it is possible to suppress the degradation in the performance of the therapeutic action and the nursing work caused by the manipulation of the medical device. Especially in environments where high cleanliness is required, such as operating rooms or neonatal intensive care units (NICU), the above-mentioned effects become more remarkable by reducing the need for the disinfecting work.

DESCRIPTION OF EMBODIMENTS

Figure 1:
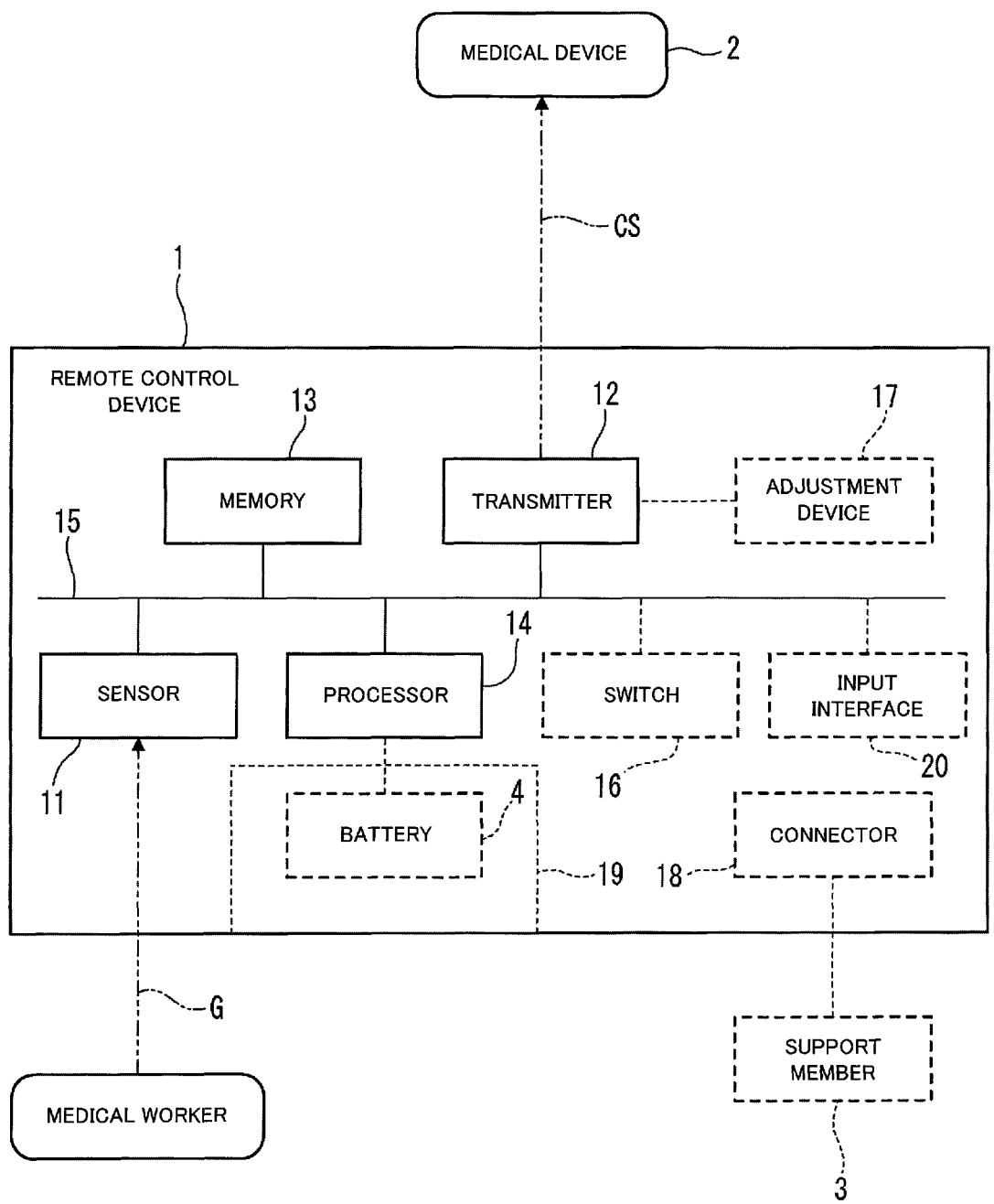
FIG. 1 illustrates a functional configuration of a remote control device according to an embodiment.
Figure 2:
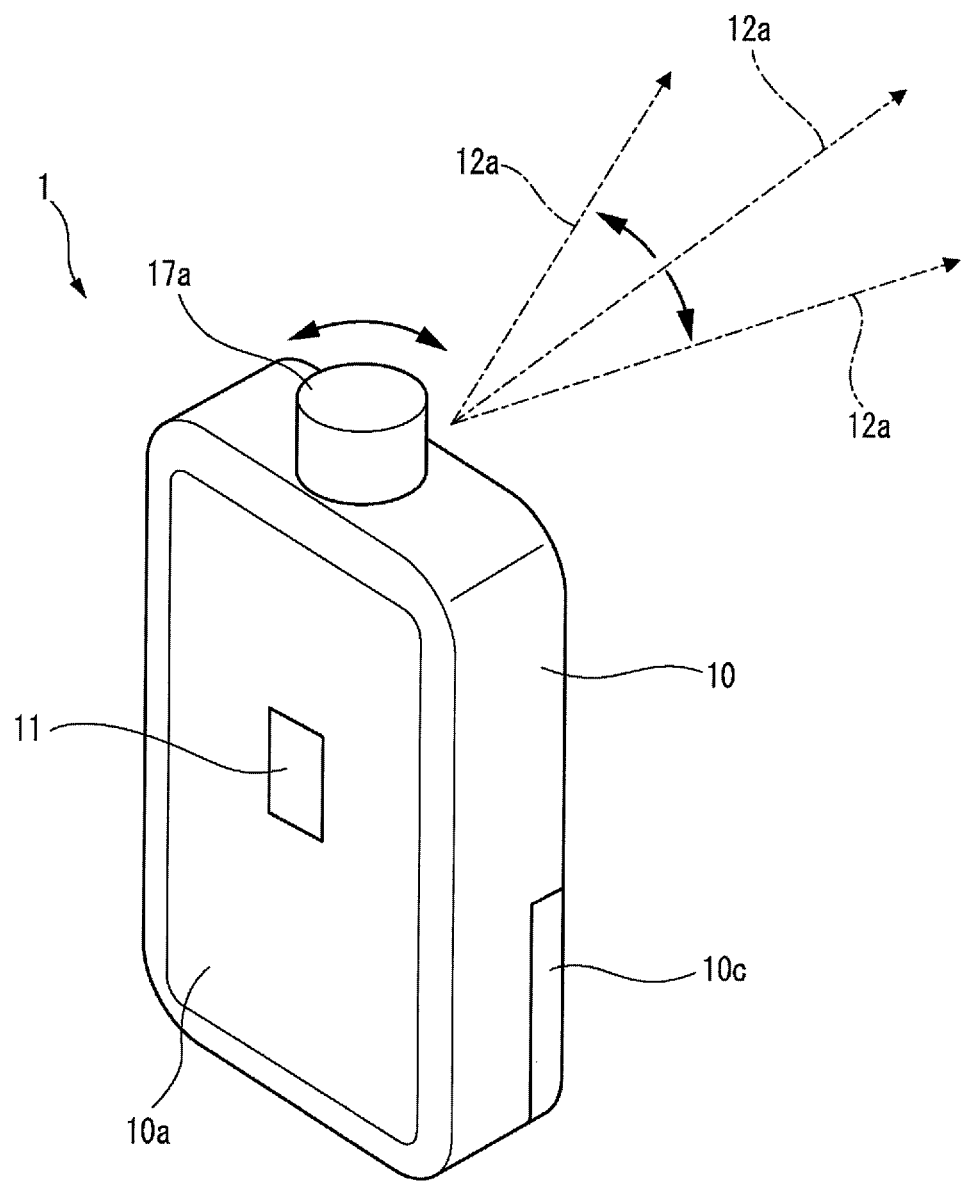
FIG. 2 illustrates an appearance of the remote control device of FIG. 1.
Figure 3:
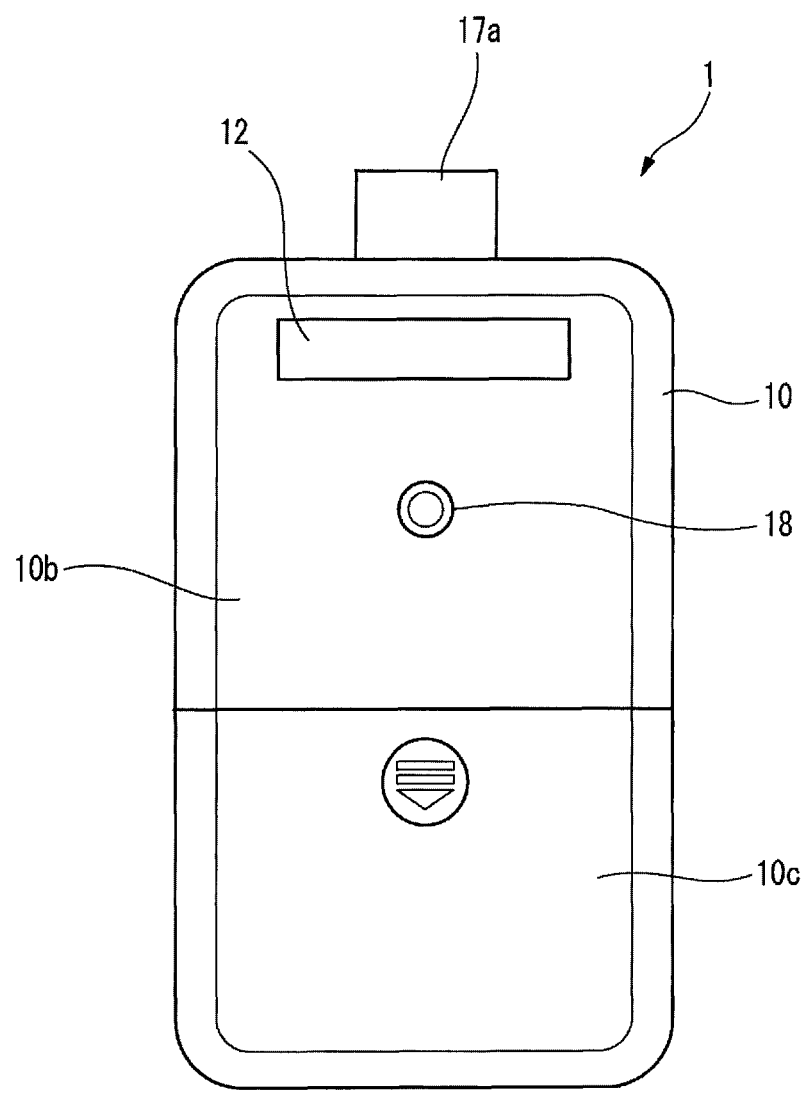
FIG. 3 illustrates an appearance of the remote control device of FIG. 1.

Examples of embodiments are described in detail below with reference to the accompanying drawings. FIG. 1 illustrates a functional configuration of a remote control device 1 according to an embodiment. FIGS. 2 and 3 illustrate an appearance including a housing 10 of the remote control device 1. The remote control device 1 is a device for remotely controlling a function of the medical device 2 at a remote location by wireless communication. The remote control device 1 and the medical device 2 may constitute a remote control system.

Examples of the medical device 2 include a vital sign information monitor and a surgery assisting apparatus such as an anesthesia apparatus and an infusion apparatus. Examples of functions of the medical device 2 include turning on/off of a power source, changing information items to be displayed on a display, changing appearances of information items to be displayed on a display, changing ways of notification such as an alarm, execute or cancel of an operation unique to the device, and changing various settings.

As illustrated in FIG. 1, the remote control device 1 includes a sensor 11. The sensor 11 is configured to detect a gesture G of a medical worker. As illustrated in FIG. 2, the sensor 11 is disposed on a front face 10a of the housing 10, for example.

As used herein, the expression "a gesture of a medical worker" refers to an action that a medical worker intentionally performs using a portion of his or her body. Examples of gestures may include holding a hand over a specific position, moving an index finger in a predetermined direction, crossing fingers of both hands, swinging a head, moving a face closer to the sensor, moving an arm up and down, raising a knee to the hip level, and the like.

The sensor 11 may be configured as a well-known sensor capable of recognizing a predetermined gesture G. For example, if only the fact that the medical worker has held his/her hand over the housing 10 needs to be detected, the sensor 11 can be implemented by a distance sensor using infrared rays or the like. If it is necessary to detect the movement direction or the movement amount of the body part of the medical worker, the sensor 11 can be implemented by a motion sensor, an imaging device, or the like.

As illustrated in FIG. 1, the remote control device 1 includes a transmitter 12. The transmitter 12 is configured to wirelessly transmit a control signal CS for controlling the function of the medical device 2. As illustrated in FIG. 3, the transmitter 12 is disposed on a rear face 10b of the housing 10, for example. The transmitter 12 may be configured as a well-known device capable of transmitting a radio signal. Examples of the wireless signal include an optical signal having predetermined wavelengths such as infra-red rays, and a radio wave signal used for wireless communication such as NFC (Near Field Communication) or Bluetooth (registered trademark) communication.

As illustrated in FIG. 1, the remote control device 1 includes a memory 13, a processor 14, and a communication bus 15. The sensor 11, the transmitter 12, the memory 13, and the processor 14 can communicate signals and data with each other via the communication bus 15. Although not illustrated, the remote control device 1 includes an appropriate signal conversion circuit that enables such communication while performing predetermined operations assigned to the sensor 11, the transmitter 12, the memory 13, and the processor 14. Examples of such a signal conversion circuit include an A/D converter, a D/A converter, and a frequency filter.

The memory 13 and the processor 14 may be a general-purpose microprocessor and a general-purpose memory cooperating with each other. Examples of the general-purpose microprocessor include a CPU and an MPU. Examples of the general-purpose memory include a ROM and a RAM. The memory 13 and the processor 14 may be implemented as a portion of a dedicated integrated circuit such as a microcomputer, an ASIC, and an FPGA.

The memory 13 stores gesture information corresponding to the gesture G of the medical worker assigned to the function of the controlled medical device 2. Specifically, the gesture information representing the output of the sensor 11 obtained by the gesture G and the control information for causing the transmitter 12 to transmit the control signal CS for stopping the alarm output of the medical device 2 are associated in the memory 13.

When a gesture G of a medical worker corresponding to the gesture information stored in the memory 13 is detected by the sensor 11, the processor 14 is configured to cause the transmitter 12 to transmit a control signal CS for controlling the function of the medical device 2 corresponding to the gesture G. Specifically, the processor 14 determines whether the signal output from the sensor 11 corresponds to the gesture information stored in the memory 13. When the correspondence is confirmed, the processor 14 determines that the gesture G for controlling the function of the medical device 2 is detected by the sensor 11. Based on the determination, the processor 14 causes the transmitter 12 to transmit a control signal CS associated with the gesture G in the memory 13.

Figure 4:
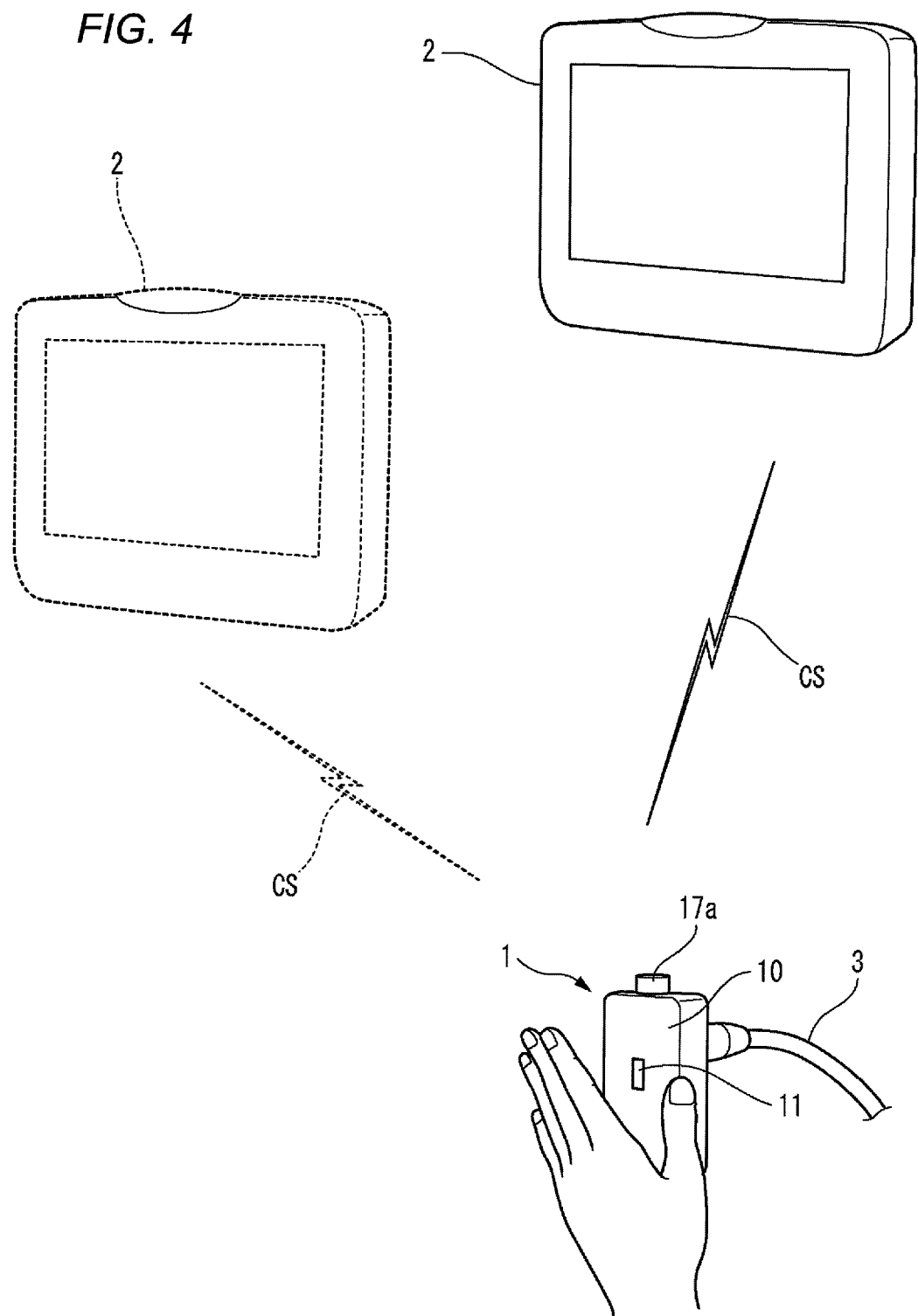
FIG. 4 illustrates an operation of the remote control device of FIG. 1.

FIG. 4 illustrates an example of the operation of the remote control device 1 configured as described above. In this example, the gesture G of the medical worker holding his/her hand over the remote control device 1 is assigned to the function for stopping the alarm output from the vital sign information monitor as the medical device 2.

When the state of the subject or patient monitored by the vital sign information monitor deviates from the normal condition, the vital sign information monitor outputs a predetermined alarm to perform the notification to the medical worker. The medical worker who has received the notification holds his/her hand over the remote control device 1. The sensor 11 detects the gesture of the medical worker and outputs a signal corresponding to the gesture. The processor 14 determines whether the signal corresponds to predetermined gesture information stored in the memory 13.

In the illustrated example, the gesture by the medical worker corresponds to predetermined gesture information stored in the memory 13. Accordingly, the processor 14 causes the transmitter 12 (not illustrated) to transmit the control signal CS for stopping the alarm output of the vital sign information monitor. The vital sign information monitor as the medical device 2 includes a receiver (not illustrated) capable of receiving the control signal CS wirelessly transmitted. The vital sign information monitor is configured to control its own operation in response to the control signal CS received by the receiver. In this example, the vital sign information monitor stops the alarm output in response to the reception of the control signal CS.

Even if a medical worker performs a gesture other than holding his/her hand over a specific position, the gesture can be detected by the sensor 11. However, the signal output from the sensor 11 according to the gesture does not correspond to the predetermined gesture information stored in the memory 13. Accordingly, the processor 14 does not determine that the sensor 11 has detected the predetermined gesture. Therefore, the control signal CS for stopping the alarm output of the vital sign information monitor is not transmitted from the transmitter 12.

According to the configuration as described above, since the remote control device 1 wirelessly transmits the control signal CS for controlling the function of the medical device 2 by sensing the gesture G of the medical worker, the medical worker can control the function of the medical device 2 with the minimum necessary action without directly touching the remote control device 1 or the medical device 2. As a result, it is possible to suppress the degradation in the performance of the therapeutic action and the nursing work caused by the manipulation of the medical device 2. Especially in environments where high cleanliness is required, such as operating rooms or neonatal intensive care units (NICU), the above-mentioned effects become more remarkable by reducing the need for the disinfecting work.

As illustrated in FIG. 1, the remote control device 1 may include a switch 16. The switch 16 may include at least one button switch, dip switch, or the like. The switch 16 may be disposed in the housing 10 or may be disposed on the outer face of the housing 10.

The switch 16 may be configured to assign a specific gesture G of a medical worker to each of a plurality of functions in the medical device 2 as gesture information, and to store the gesture information in the memory 13.

Figure 5:
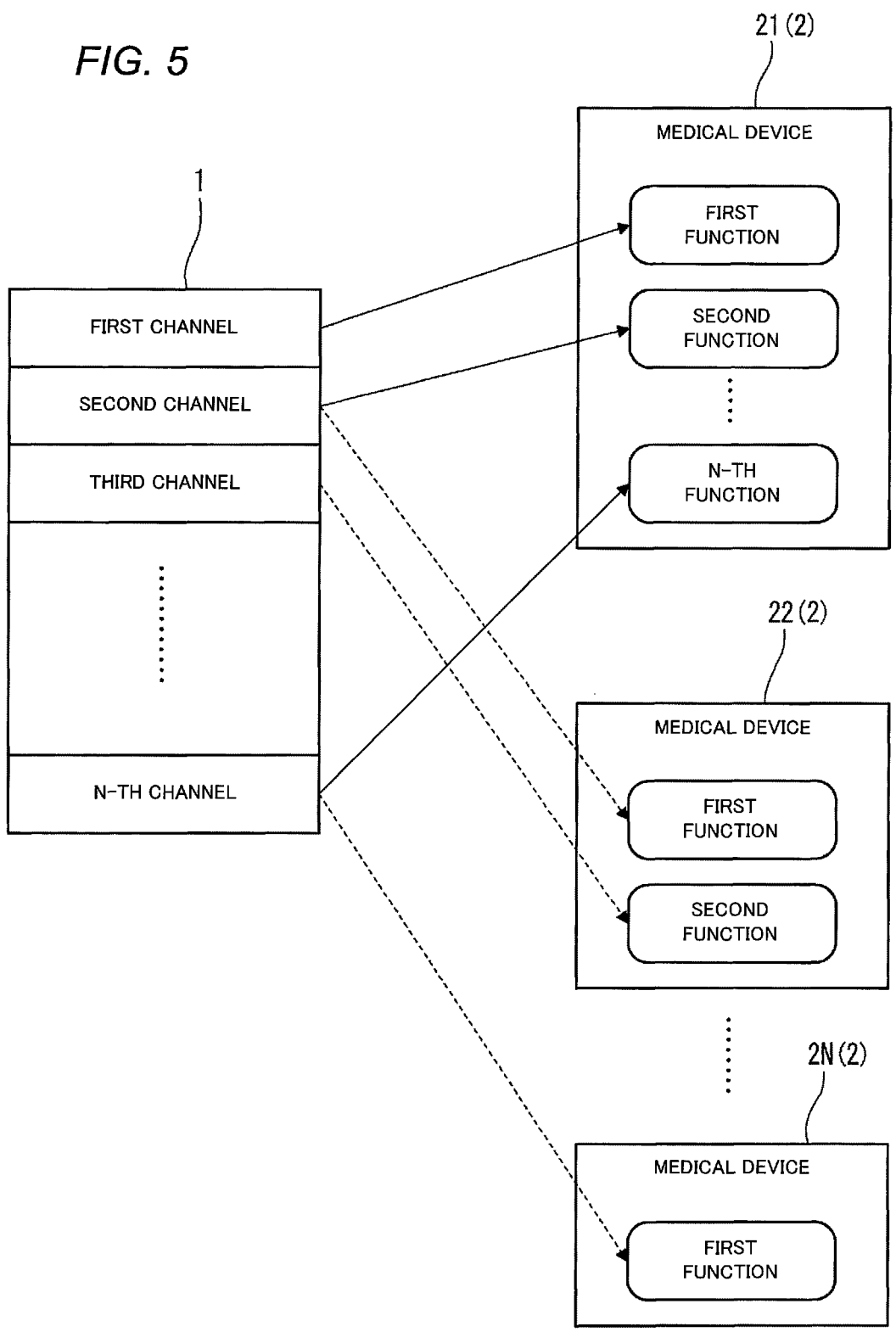
FIG. 5 illustrates an operation of the remote control device of FIG. 1.

For example, as illustrated in FIG. 5, a plurality of channels can be provided in the remote control device 1 according to the state of the switch 16. In the illustrated example, N channels are provided. The first channel, the second channel, and the N-th channel are respectively assigned to the first function, the second function, and the N-th function of the medical device 21. The first function is, for example, a function for stopping an alarm output. The second function is, for example, a function of turning on a power source. The N-th function is, for example, a function to turn off the power source.

A particular gesture of a medical worker may be assigned to each of the N channels. For example, a "holding a hand over a specific position" gesture may be assigned to the first channel, a "moving a hand upward" gesture may be assigned to the second channel, and a "moving a hand downward" gesture may be assigned to the N-th channel.

The assignment of such a gesture can be performed, for example, by the following procedure.

The learning mode is enabled by inputting a predetermined instruction to the remote control device 1.

The switch 16 is operated to set a state corresponding to a specific channel.

The sensor 11 is caused to detect a gesture desired to be assigned to the channel.

The learning mode is terminated by inputting a predetermined instruction to the remote control device 1.

As a result, the output signal of the sensor 11 corresponding to the specific gesture is allocated to the specific channel as gesture information to be stored in the memory 13 for each channel.

After such a setting operation is performed, for example, when the sensor 11 detects a gesture of "moving a hand downward" by a medical worker, the processor 14 causes the transmitter 12 to transmit a control signal CS for turning off the power of the medical device 21. As a result, the power of the medical device 21 located remotely from the remote control device 1 is turned off.

According to such a configuration, the medical worker can control a plurality of functions of the medical device 2 without directly touching the remote control device 1 or the medical device 2. As a result, the effect of suppressing the degradation in the performance of the therapeutic action and the nursing work caused by the manipulation of the medical device 2 is enhanced.

Additionally or alternatively, the switch 16 may be configured to assign a particular gesture G of a medical worker to a particular function in each of a plurality of medical devices 21, 22, . . . , 2N as the gesture information, and to store the gesture information in the memory 13.

For example, as illustrated in dashed lines in FIG. 5, the first channel, the second channel, and the N-th channel are assigned to the first function of the medical device 21, the first function of the medical device 22, and the first function of the medical device 2N, respectively. The first function is, for example, a function for stopping an alarm output.

Also in this case, a particular gesture of the medical worker may be assigned to each of the N channels. For example, a "holding a hand over a specific position" gesture may be assigned to the first channel, a "moving a hand upward" gesture may be assigned to the second channel, and a "moving a hand downward" gesture may be assigned to the N-th channel. The assignment of the gesture may be performed in the procedure described above.

After such a setting operation is performed, for example, when the sensor 11 detects a gesture of "moving a hand downward" by a medical worker, the processor 14 causes the transmitter 12 to transmit a control signal CS for causing the medical device 2N to stop the alarm output. As a result, the alarm output of the medical device 2N located remotely from the remote control device 1 is stopped.

According to such a configuration, the medical worker can control the functions of the plurality of medical devices 2 without directly touching the remote control device 1 or the medical devices 2. As a result, the effect of suppressing the degradation in the performance of the therapeutic action and the nursing work caused by the manipulation of the medical device 2 is enhanced.

In a case where the functions of a plurality of medical devices 2 are controlled by a single remote control device 1, the number of functions to be controlled in each medical device can be appropriately determined. In the example illustrated in FIG. 5, the third channel of the remote control device 1 is allocated to the second function of the medical device 22. That is, two functions can be remotely controlled in the medical device 22.

In each of the examples described above, the remote control device 1 controls the function for stopping the alarm output of the medical device 2. The function for stopping the alarm output is an example of a function for restricting the alarm output. The function for restricting the alarm output may include a function for suspending the alarm output for a predetermined time period or a function for disabling the alarm output.

When an alarm is output from the medical device 2, it is highly probable that the medical worker is in a situation in which an urgent response is required. According to the above-described configuration, it is possible to suppress the degradation in the performance of the therapeutic action or the nursing work caused by the manipulation of the medical device 2 under such a situation, so that it is possible to support the urgent response by the medical worker.

As illustrated in FIG. 1, the remote control device 1 may include an adjustment device 17. The adjustment device 17 is a device for changing the direction in which the control signal CS is transmitted from the transmitter 12. For example, as illustrated in FIGS. 2 and 3, the adjustment device 17 may include a knob 17a disposed on the housing 10. The knob 17a may be coupled to a transmitter 12 disposed in the housing 10. In this case, the medical worker can change the direction of a transmission center axis 12a of the transmitter 12 illustrated in FIG. 2 by rotating the knob 17a. The transmission center axis 12a is an axis extending in an angular direction in which a signal strength of the control signal CS transmitted from the transmitter 12 is the strongest.

For example, the medical device 2 illustrated by the dashed lines in FIG. 4 is not positioned on the extension of the transmission central axis 12a in the initial state. In such a case, the medical worker can adjust the transmission center axis 12a to face the medical device 2 illustrated by the dashed lines by rotating the knob 17a of the adjustment device 17. As a result, the control signal CS indicated by the dashed lines transmitted from the transmitter 12 is transmitted toward the medical device 2 indicated by the dashed lines.

According to such a configuration, the positional relationship between the remote control device 1 and the medical device 2 can be determined with a relatively high degree of freedom in accordance with the layout of the place where the remote control device 1 and the medical device 2 are installed as well as the operation routes of the medical workers. As a result, the effect of suppressing the degradation in the performance of the therapeutic action and the nursing work caused by the manipulation of the medical device 2 is enhanced.

As illustrated in FIG. 1, the remote control device 1 may include a connector 18. The connector 18 is configured to be attached, in a detachable manner, to a support member 3 for fixing the housing 10 of the remote control device 1 to a desired position. For example, as illustrated in FIG. 3, the connector 18 may be a threaded hole formed in a back face 10b of the housing 10. The threaded hole may be in compliance with, for example, the ¼-20 UNC Unified Screw Standard. The support member 3 is provided with a threaded portion that fits into the threaded hole, a clamp that can be fixed to a desired position, and the like. FIG. 4 illustrates a state in which the support member 3 is coupled to the housing 10 of the remote control device 1.

According to such a configuration, the degree of freedom in determining the arrangement of the remote control device 1 is increased. As a result, the effect of suppressing the degradation in the performance of the therapeutic action and the nursing work caused by the manipulation of the medical device 2 is enhanced.

As illustrated in FIG. 1, the remote control device 1 may include a battery housing 19. The battery housing 19 is configured to house a battery 4 for supplying power to at least the processor 14. For example, as illustrated in FIGS. 2 and 3, a detachable battery lid 10c may be attached to the back face 10b of the housing 10. By removing the battery lid 10c, the battery housing 19 can be opened. The battery accommodated in the battery housing 19 may be a primary battery or a secondary battery.

According to such a configuration, it is not necessary to consider the positional relationship with a commercial power supply connected via a cable, so that the degree of freedom in determining the arrangement of the remote control device 1 is increased. As a result, the effect of suppressing the degradation in the performance of the therapeutic action and the nursing work caused by the manipulation of the medical device 2 is enhanced.

The remote control device 1 and the medical device 2 may have a pairing function for establishing a control-controlled relationship. For example, as illustrated in FIG. 1, the remote control device 1 may include an input interface 20. The medical worker inputs information identifying the medical device 2 controlled by the control signal CS through the input interface 20. Additionally or alternatively, a similar input interface may be provided on the medical device 2 side. In this case, the medical worker inputs information specifying the remote control device 1 that transmits the control signal CS through the input interface. Thus, the pairing between the remote control device 1 and the medical device 2 is established based on the information inputted to at least one of the remote control device 1 and the medical device 2.

According to such a configuration, remote control is enabled only between the specific remote control device 1 and the medical device 2 for which pairing has been established. Therefore, it is possible to avoid a situation in which a medical device other than the specific medical device 2 is operated unexpectedly by the control signal CS transmitted from the remote control device 1.

The above embodiment is merely exemplary to facilitate understanding of the presently disclosed subject matter. The configuration according to the above embodiment can be appropriately modified or improved without departing from the fundamental concept of the presently disclosed subject matter.

In the embodiment described above, the gesture of the medical worker is detected by the sensor 11. Additionally or alternatively, the voice and/or the physical feature of the medical worker may be detected by the sensor 11. As the physical feature a retina, a fingerprint, a face or the like can be exemplified. In this case, the sensor 11 may be implemented by a voice recognition sensor, a fingerprint sensor, a retinal sensor, or the like. Even with such a configuration, the function of the medical device 2 can be remotely controlled by using a non-contact input to the remote control device 1 as a trigger.

The present application is based on Japanese Patent Application No. 2018-184191 filed on Sep. 28, 2018, the entire contents of which are hereby incorporated by reference.

The invention claimed is:

1. A remote control device comprising:
   a memory storing information corresponding to a gesture of a medical worker that is allocated to a function of a medical device;
   a sensor configured to detect a gesture;
   a transmitter configured to wirelessly transmit a signal for remotely controlling the function;
   a physical switch configured to assign a gesture of a medical worker to each of a plurality of functions of the medical device as the information, and to cause the memory to store the information,
   a plurality of channels, and
   a processor configured to:
   identify, based on the information stored in the memory, a function of the medical device being controlled by the gesture, in a case where the gesture corresponding to the information is detected by the sensor; and
   cause the transmitter to transmit the signal for remotely controlling the function,
   wherein the physical switch includes a button switch or a dip switch;
   wherein the physical switch being configured to assign the gesture of the medical worker to each of the plurality of functions of the medical device as the information includes being configured to assign each of the plurality of channels to a corresponding function of the plurality of functions; and
   wherein the physical switch being configured to assign the gesture of the medical worker to each of the plurality of functions of the medical device as the information also includes being configured to:
   enable a learning mode of the remote control device,
   operate the physical switch to set a state of a specific channel of the plurality of channels,
   detect a particular gesture of the gesture by the sensor,
   assign the particular gesture to the specific channel, and
   disable the learning mode of the remote control device.

2. The remote control device according to claim 1, wherein the function is a function for restricting an alarm output.

3. The remote control device according to claim 1, comprising:
an adjustment device configured to change a direction in which the signal is transmitted.

4. The remote control device according to claim 1, comprising:
a housing provided with a connector,
wherein the connector is configured to be attached, in a detachable manner, to a support member configured to fix the housing to a desired position.

5. The remote control device according to claim 1, comprising:
a battery housing configured to house a battery configured to supply power to at least the processor.

6. The remote control device according to claim 1, comprising:
an input interface configured to input information for specifying a medical device to be controlled by the signal.

7. A remote control system comprising:
a medical device; and
a remote control device configured to remotely control a function of the medical device,
wherein the remote control device comprises:
a memory storing information corresponding to a gesture of a medical worker that is allocated to the function;
a sensor configured to detect a gesture;
a transmitter configured to wirelessly transmit a signal for remotely controlling the function;
a physical switch configured to assign a gesture of a medical worker to each of a plurality of functions of the medical device as the information, and to cause the memory to store the information;
a plurality of channels; and
a processor configured to:
identify, based on the information stored in the memory, a function of the medical device being controlled by the gesture, in a case where the gesture corresponding to the information is detected by the sensor; and
cause the transmitter to transmit the signal for remotely controlling the function, and wherein the physical switch includes a button switch or a dip switch;
wherein the physical switch being configured to assign the gesture of the medical worker to each of the plurality of functions of the medical device as the information includes being configured to assign each of the plurality of channels to a corresponding function of the plurality of functions; and
wherein the physical switch being configured to assign the gesture of the medical worker to each of the plurality of functions of the medical device as the information also includes being configured to:
enable a learning mode of the remote control device,
operate the physical switch to set a state of a specific channel of the plurality of channels,
detect a particular gesture of the a gesture by the sensor,
assign the particular gesture to the specific channel, and
disable the learning mode of the remote control device.

8. The remote control system according to claim 7,
wherein at least one of the remote control device and the medical device comprises an input interface configured to input information for establishing a control-controlled relationship between the remote control device and the medical device.

9. A remote control device comprising:
a memory storing information corresponding to a gesture of a medical worker that is allocated to a function of a medical device;
a sensor configured to detect a gesture;
a transmitter configured to wirelessly transmit a signal for remotely controlling the function;
a physical switch configured to assign a gesture of a medical worker to each of a plurality of functions of the medical device as the information, and to cause the memory to store the information;
a plurality of channels; and
a processor configured to:
identify, based on the information stored in the memory, a function of the medical device being controlled by the gesture, in a case where the gesture corresponding to the information is detected by the sensor; and
cause the transmitter to transmit the signal for remotely controlling the function,
wherein the physical switch includes a button switch or a dip switch;
wherein the physical switch being configured to assign the gesture of the medical worker to each of the plurality of functions of the medical device as the information includes being configured to assign each of the plurality of channels to a corresponding function of the plurality of functions; and
wherein the physical switch being configured to assign the gesture of the medical worker to each of the plurality of functions of the medical device as the information also includes being configured to:
enable a learning mode of the remote control device,
operate the physical switch to set a state of a specific channel of the plurality of channels,
detect a particular gesture of the a gesture by the sensor,
assign the particular gesture to the specific channel, and
disable the learning mode of the remote control device; and
wherein the physical switch is further configured to cause the memory to store the information.

* * * * *